United States Patent [19]

Wood

[11] Patent Number: 4,887,463
[45] Date of Patent: Dec. 19, 1989

[54] PAVEMENT TESTING MACHINE AND METHOD OF TESTING PAVEMENTS

[76] Inventor: William I. Wood, 59 Memorial Avenue Fendalton, Christchurch, New Zealand

[21] Appl. No.: 117,521

[22] Filed: Nov. 2, 1987

[51] Int. Cl.⁴ ............................................. E01C 23/00
[52] U.S. Cl. ........................................... 73/146; 73/8
[58] Field of Search ........................... 73/8, 146, 9, 104

[56] References Cited

U.S. PATENT DOCUMENTS 3,119,257  1/1964  Speer ..................................... 73/146
4,502,327  3/1985  Scrivener et al. ..................... 73/146

OTHER PUBLICATIONS

Van Vuuren, D. J., "The Heavy Vehicle Simulator", Shell Review, vol. 41, (1973).
Pidwersky, Horosko, Wood & Bergman, "Indoor Pavement Test Tracks Incorporating Advanced Technology".
Brown & Brodrick, "Nottingham Pavement Test Facility", U.K. Transportation Research Report 810.
Burgstaller et al., "Dynamic Deflection Measurements Under Moving Wheel Loads", International Symposium on Bearing Capacity of Roads and Air Fields, Jun. 23-25, 1982, Tromdheim, Norway.

*Primary Examiner*—Donald O. Woodiel
*Attorney, Agent, or Firm*—Pasquale A. Razzano

[57] ABSTRACT

An apparatus for testing and evaluating traffic bearing formation and pavements includes one or more arms extending radially from a center pivot, each arm being adapted to connect to a bogey comprising one or more wheels and to constrain its respective bogey to movement in a generally circular path on the pavement about a pivot during operation of the apparatus; a plurality of bogies, each adapted to be coupled to an arm and comprising differing combinations of one or more multiple wheels so as to each represent an actual wheel or wheel set of a vehicle; a wheel suspension system for each bogey constraining the wheel or wheels thereof to move such that the dynamic responses of the wheel or wheels to pavement irregularities substantially replicate the dynamic response of actual vehicle wheels to actual roadway irregularities; a driving system for the wheels adapted to apply tractive and braking efforts thereto for the vehicle type which any wheel set represents, the road speed of the wheel on the pavement being variable between zero and a maximum speed; and an electronic control system for the apparatus arranged to control functions thereof including the driving system to said wheels and the speed and tractive end braking efforts applied thereto.

32 Claims, 8 Drawing Sheets

PAVEMENT TESTING MACHINE AND METHOD OF TESTING PAVEMENTS

The present invention relates to a machine for testing pavements such as paved surfaces and in particular, roads, highways, aircraft runways and the like for the purpose of evaluating the performance and the durability of paved surfaces and substrates and surfacings under controlled conditions.

An object of he present invention is the provision of a pavement testing machine which can replicate actual road traffic conditions, e.g. by simulating speed, accelerating and braking, wheel or axle loadings and which can replicate actual road conditions on a test road pavement, e.g. by distributing traffic to a realistic pattern or simulating road gradients. Thus the data gathered by testing road formations and surfacings with this machine may be applied directly to the design of highways, aircraft runways and other traffic bearing surfaces.

Another object of the present invention is the provision of a method of testing and evaluating the durability of road surfaces, substrates and formations efficiently and safely.

A further object of the present invention is the provision of a pavement testing machine which efficiently and safely evaluates and tests the durability of road formations, surfaces and substrates in a manner that reduces the energy or power requirements of the pavement testing machine.

In one aspect the invention comprises apparatus for testing pavements including means adapted to rotate about a central pivot and having at least one arm extending radially from said central pivot, the outer end of said arm carrying a driven road wheel to contact the paved surface; said machine including means to provide a force to rotate or resist the rotation of the radial arm about the central pivot, means being also provided to vary the vertical forces between the road wheel and the paved surface and the configuration of road wheels.

The present invention may also be said to comprise a machine for testing pavements, said machine including: a fixed centre post assembly engaging a rotatable centre pin, a bolster attached to said rotatable centre pin and housing a slide frame which has radial movement in relation to the bolster; a radial arm connected by one end in a substantially horizontal plane to one end of the said slide frame; a road wheel bogey connected to the second end of said radial arm; a first driving means mounted on said bolster for rotating the radial arm about the bolster; a subsidiary driving means connected to the road wheel and to the first driving means to produce acceleration, braking and constant speed; a retarding means to simulate the effect of road gradients connected with the first driving means to provide resistive force to the rotation of the said radial arm about the bolster; means to recover and reuse a portion of the energy consumed; and means to apply differing wheel loads to said road wheel bogey and to connect bogies with differing wheel arrangements.

Preferably, the first driving means is a variable volume hydraulic pump directly coupled to an electric motor. Preferably a second driving means is a small volume regulated pump directly coupled to an electric motor. Also, the subsidiary driving means are preferably hydraulic motors functioning in the fixed displacement mode, and the retarding means is a second variable displacement hydraulic pump mounted on the bolster section and driven from a gear wheel mounted on the fixed centre post assembly.

Preferably two radial arms are attached to the slide frame and are disposed diametrically opposite each other about the centre post assembly. Each road wheel bogey preferably is capable of containing one axle carrying a single or a dual tired truck wheel assembly, or may contain two axles and dual tired wheels. One or more supplementary wheels which typically equate to light vehicle wheels may be attached through brackets to the bogies.

The present invention further provides a method of testing and evaluating the performance and durability of road formations, substrates and surfacings, said method comprising: arranging a predetermined number of wheels and axles in the bogies of said pavement testing machine; arranging a predetermined loading on said bogey wheels; distributing wheel traffic over the test pavements to a predetermined pattern; providing safety devices and cutout mechanisms for monitoring the safe operation of the said pavement testing machine, providing a control system for operating said machine including means to cause the pavement testing machine to perform a predetermined regime of functions and a means to operate the safety devices and cut out mechanisms; and providing a monitoring system for monitoring and recording the performance of said pavement testing machine, the road surface conditions and the safety devices. The predetermined regime of functions includes simulation of acceleration, braking, running at a steady speed, climbing and descending a gradient, varying the distribution of wheel traffic over the breadth of a test pavement, or any combination thereof, stopping, starting at predetermined times and running the pavement testing machine for a predetermined time or predetermined distance, or any combination thereof. The duration of such testing regimes may extend over periods of days or weeks during which the machine operates without human attendance, records its operating and testing data and may be monitored or interrogated by a conventional telephone link from points which are remote from the test site.

The present invention further provides an energy recuperation system which may be applied to a machine which utilizes hydraulic driving means, said system comprising: the extraction of energy from said machine when said machine is in a braking mode which is concurrent with a driving mode in the same or in a separate hydraulic loop; and the re-introduction of said energy into the hydraulic power system to augment the external driving power.

By way of example only, a preferred embodiment of the present invention will be described with reference to and as shown in the accompanying drawings in which.

Figure 1:
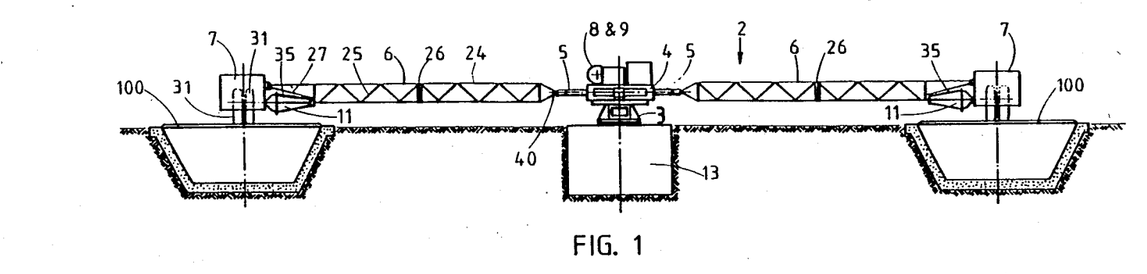
FIG. 1 is a side view of the machine showing only one radial arm also showing a typical test pavement
Figure 2:
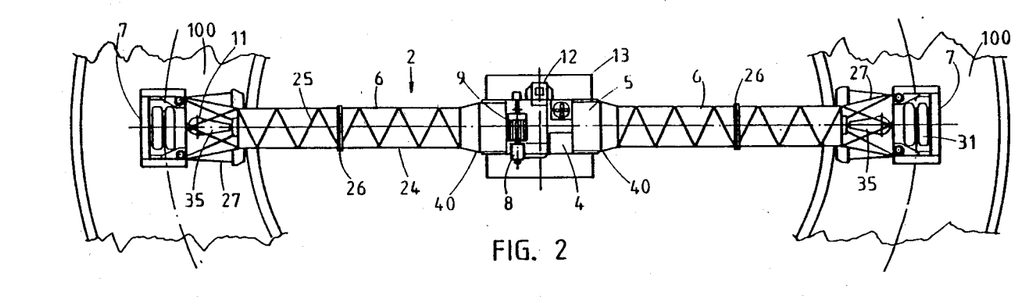
FIG. 2 is a plan view of the machine as shown in FIG. 1 and part of the surface of a test track.
Figure 3:
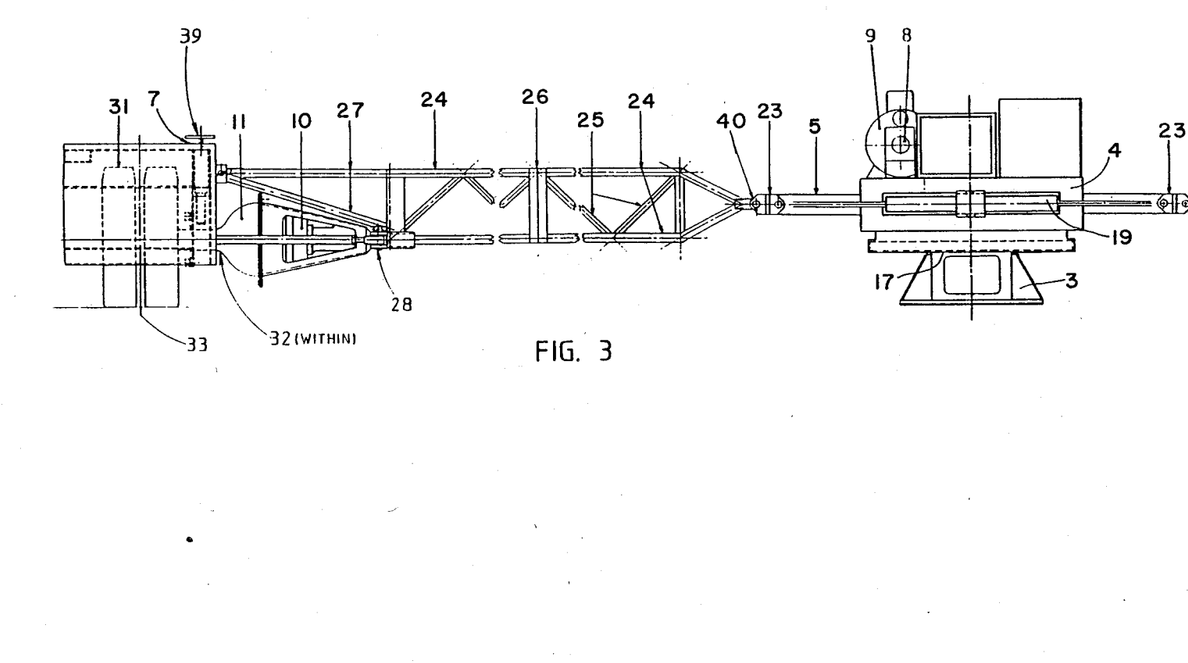
FIG. 3 is a side view of machine of the present invention showing a partial view of radial arm and its associated componentry.

Referring to the drawings and particularly to FIGS. 1 and 2, the machine has a fixed centre post assembly 3, to which is rotationally attached a rigid bolster 4 which houses a double ended slide frame 5, (see more particularly FIG. 3). Two opposed articulated radial arms 6 are connected at their inner ends by horizontal hinges 40 one to each end of the slide frame 5, and a road wheel bogey 7 is connected by a system of struts 27 to the outer end of each arm 6. A first variable volume hydraulic pump 8 is attached to the bolster 4 above the slide frame 5 and is connected to an electric motor 9 which is also mounted on the bolster 4 above the slide frame 5. A hydraulic motor 10, which functions in the fixed displacement mode, is mounted in the axle housing 11 of each road wheel bogey 7. A second variable displacement hydraulic pump 12 is rigidly mounted on the bolster 4 above the slide frame 5.

Figure 5:
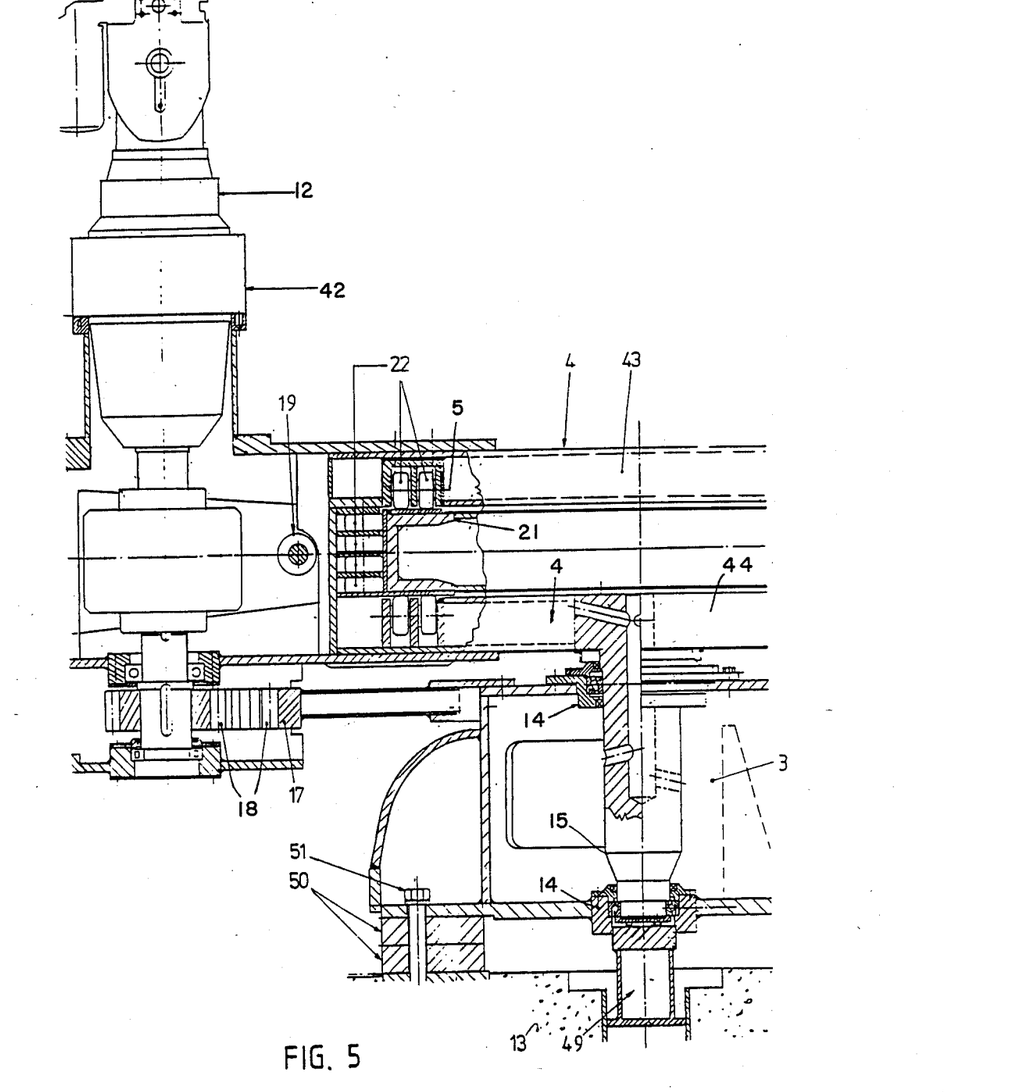
FIG. 5 is a sectional view of part of the fixed centre post and bolster assembly.

As shown in FIG. 5 the fixed centre post assembly 3 is bolted to a central foundation 13 and contains two bearings 14 one situated in the base and the other on the top of the assembly 3. A central shaft 15 is hollow and carries electrical and control cables. The assembly 3 also contains electrical slip rings (not shown) for the transmission of power and control data to and from the pavement testing machine 2.

A main gear ring 17 is rigidly attached in a substantially horizontal position to the centre post assembly 3 and positioned below the bolster 4. A pinion 18, attached to the input shaft of the second hydraulic pump 12 engages the main gear ring 17, thus providing a driving means for said pump 12. A gear box 41, attached to the bolster 4 is coupled to the main gear ring 17, and engages the second hydraulic pump 12 via a second gear box 42, thus providing driving means for said pump 12.

The bolster 4 includes a rigid top frame 43 and a rigid bottom frame 44, both lying in a substantially horizontal plane and being preferably rectangular in plan and in cross-section. The top and bottom frames 43, 44 are rigidly connected together at the four corners of the bolster 4. The slide frame 5 within the bolster 4 is powered by two hydraulic rams 19 (see FIG. 8) which are positioned in a substantially horizontal plane one on each side of the centre post assembly 3 between the ends of the slide frame 5. The hydraulic rams 19 impose radial movement about the centre post assembly 3 of the slide frame 5 in a substantially horizontal plane within the bolster 4. The hydraulic rams 19 may be driven by a volume controlled pump 20 attached to the bolster 4 and coupled to the electric motor 9.

Figure 8:
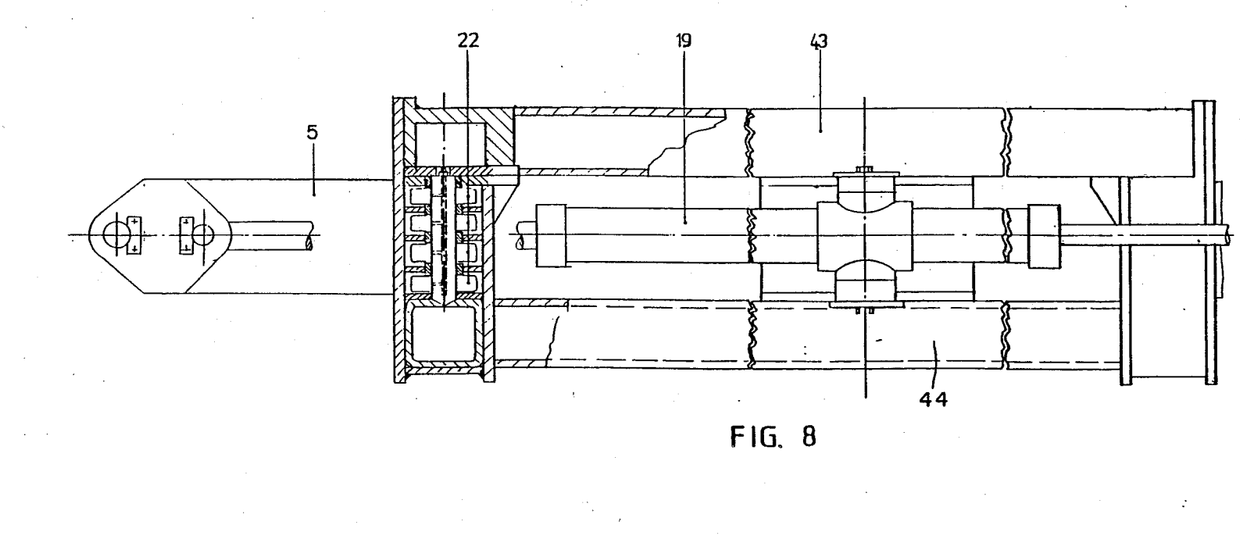
FIG. 8 is a partly cut away section view of the bolster, slide frame and slide frame actuating rams.

The slide frame 5 includes stiffened and reinforced corner members 21. The braking or acceleration of the pavement testing machine 2 imposes torsion on the slide frame 5 and this torsion, plus gradient forces and any other forces on the slide frame 5 resulting from the rotation of the pavement testing machine 2 are borne by four nests of rollers 22 one about each corner of the slide frame 5. The rollers 22 are positioned between the slide frame corner members 21 and the bolster 4, and on the top and directly underneath the slide frame corners 21, between the slide frame ends 23 and the bolster frame 43/44.

The two opposed articulated radial arms 6 are each constructed of four main chords 24 and braces 25 of a rigid material. A lockable double hinge 26 is set in approximately the middle of each arm 6 in order to enable movement of the road wheel bogey 7 to and from the pavement 100 being tested or being relayed.

A sensitive strain gauge (not shown) of known type is attached preferably to one of the braces 25 on each radial arm 6. This gauge is set to gauge the stress on the arm 6 when compared with a pre-set maximum stress limit. If this pre-set limit is approached by a predetermined amount, power to the electric motor 9 is cut-off.

Figure 4:
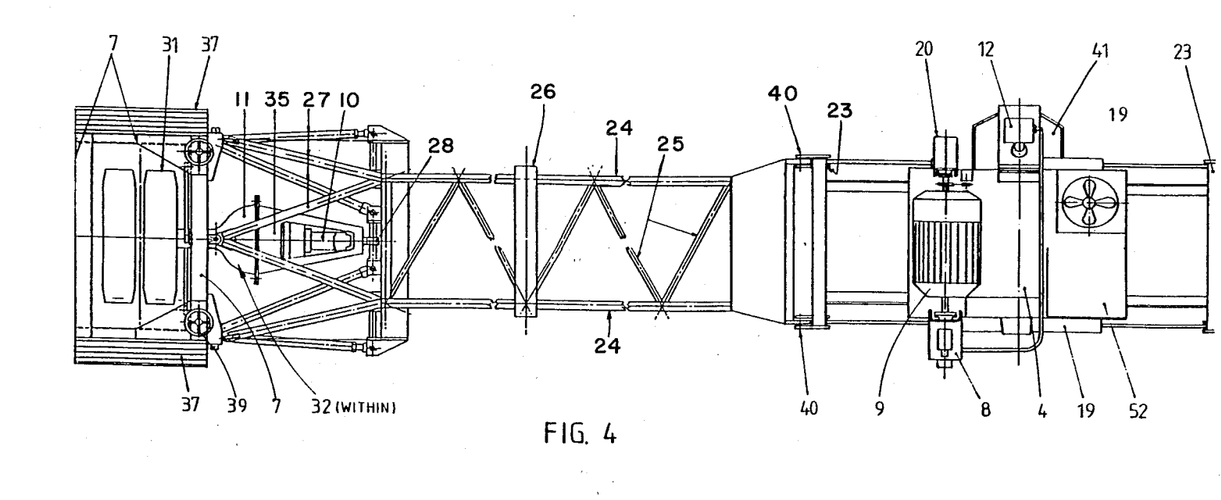
FIG. 4 is a plan view of the machine as shown in FIG. 3.

Each road wheel bogey 7 (see particularly FIG. 4) is connected to each radial arm 6 by a system of struts 27 and an axle arrangement 32 connects at a pivot point 28. The pivot point 28 contains a spherical bearing 29 and a worm wheel and screw 30 (see FIG. 6) to allow the wheels 31 to move in a vertical plane and for angular adjustment of the wheels 31 and axle 33 in the horizontal plane. This latter adjustment allows a limited variation in the slip angle of the wheels 31 relative to the pavement 100. The distance between centre line 33 and said pivot point 28 preferably corresponds with a typical track width of a motor vehicle. The axle 32 is constrained to move in a vertical path by a Watts linkage 34 which gives controlled rotational movement of the wheel 31 and axle housing 11 in a vertical plane to reproduce the effect of one wheel of full truck axle assembly passing over a road surface irregularity. The unsprung weight on the wheel 31 and the road springs 38 are preferably arranged so as to be typical for a standard motor truck to enable the combination to produce test pavement reactions which typify actual highway reactions caused in this example, by loaded truck traffic.

Figure 6:
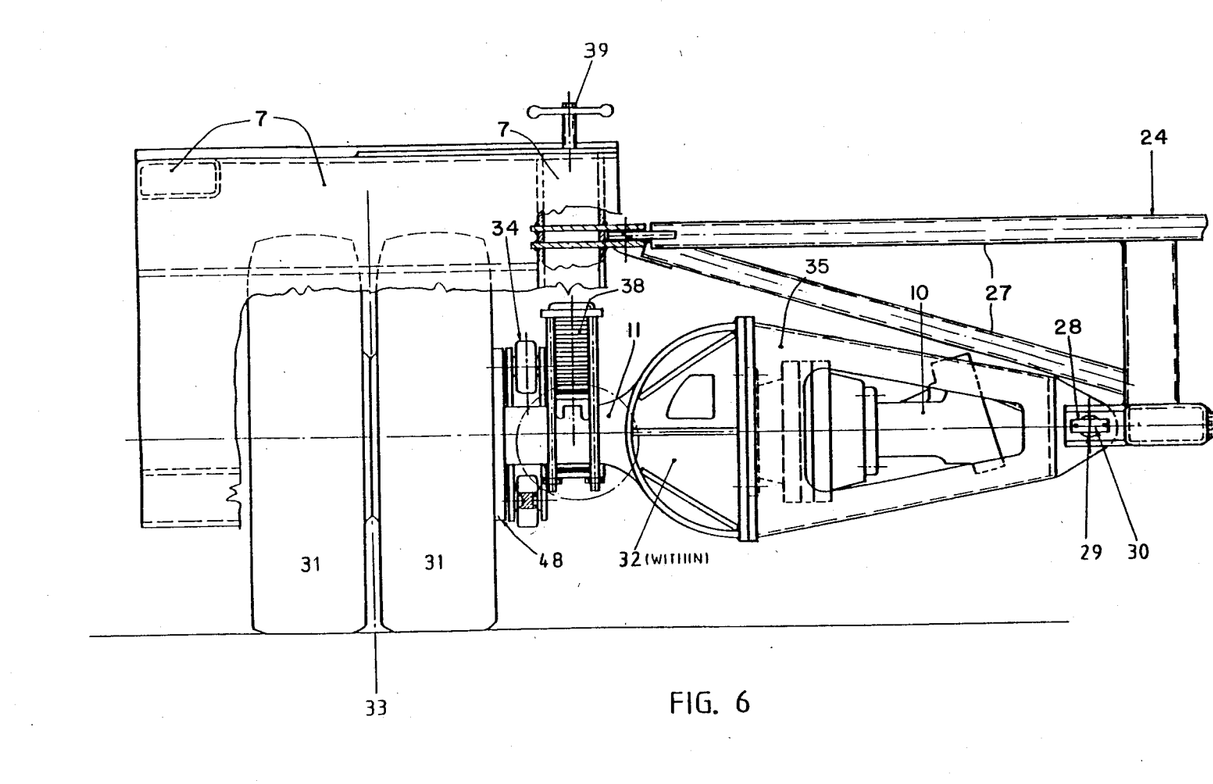
FIG. 6 is a partially cut away side view of one of the road wheel bogies.

Each bogey 7 may have one axle 32 carrying two wheels 31, and preferably the inner of which is fixed to the driving axle with the outer wheel being free to rotate separately. The above described axle configuration and wheel attachment provides a means for preventing horizontal shear forces in the pavement 100 which would result from rigidly connected dual wheels 31 which are constrained to move in a circular path. Optionally the dual wheels 31 can be rigidly connected together for the purpose of evaluating the effect of such shear forces on bends in a highway. Optionally also, a differential system may be contrived to fit between pairs of dual wheels such that the tractive effort is divided evenly to each wheel while still enabling each of the two wheels to rotate at slightly differing speeds, one to the other.

Each road wheel bogey 7 includes a sole bar 36 to which weights 37 (see FIG. 7) may be attached to adjust the axle load. A standard truck spring set 38 is positioned on each axle 32 but is not rigidly attached to the sole bar 36 or axle 32. A spring adjuster 39 bears down on each end of each spring set 38 and is used to compensate for vertical depression of the spring set 38 when weights 37 are added to the sole bar 36, thus maintaining mean horizontal alignment of pavement surface and axle for differing axle loads.

Figure 7:
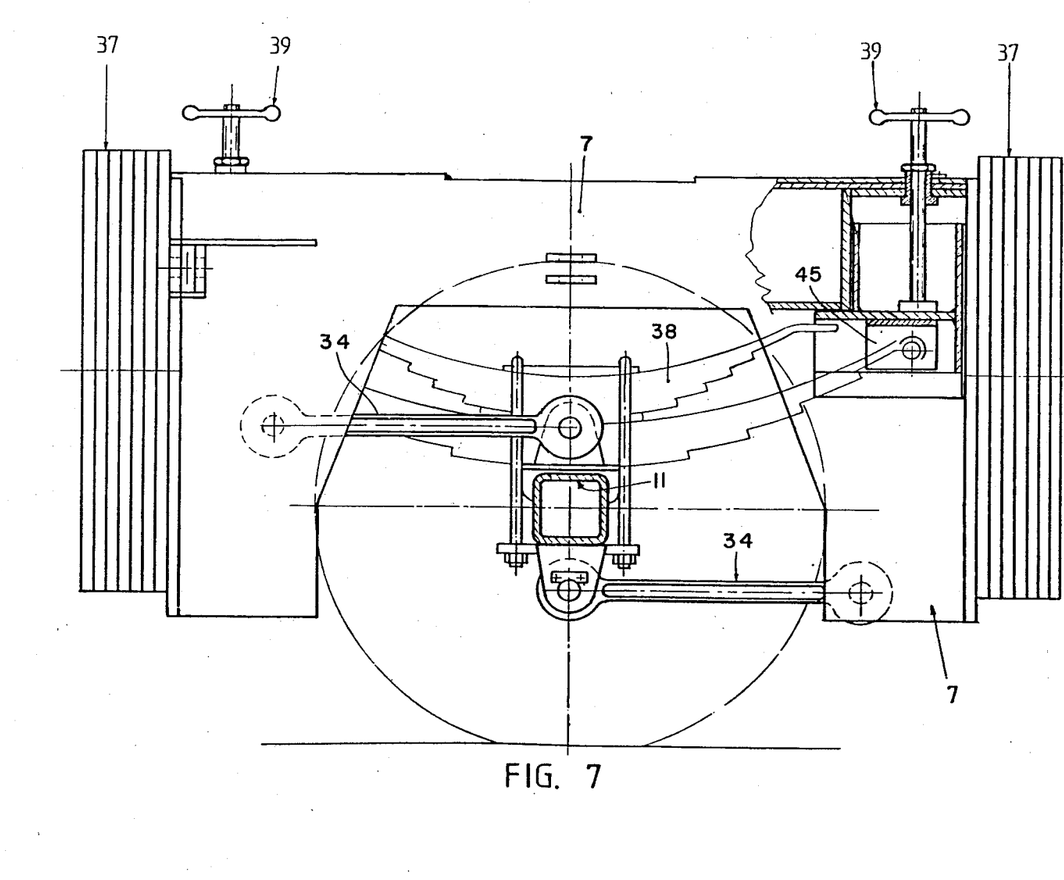
FIG. 7 is a section view along line A.A of FIG. 6.

The placement of weights 37 in respect of the fixed mass of the radial arms 6, bogey frame 7 and axle assembly 10,11,31,35, is such that the dynamic forces developed by these several masses when rotating, will remain balanced about the plane of restraint and thus prevent variation with road speed of the vertical force to be supported by the pavement.

In order to keep each spring set 38 in position on each axle 32 and preserve a mean horizontal axle alignment and an even distribution of load between the tires 31, two spring slipper arrangements 45 within the sole bar 36 each contain one end of each spring set 38. Each spring adjuster 39 bears directly on one spring slipper arrangement 45. The spring slipper arrangements 45 permit limited movement of the end of each spring set 38 in a substantially horizontal plane whilst at the same time keeping each spring set 38 in the correct position on each axle 32.

Axle displacement transducers (not shown) attach to the sole bars 36 and connect to the axle housings 11 to monitor and transmit vertical axle movements relative to bogie frames. This transmission is interpreted to present a readout of road profile and to sense a road surface break up which will stop the machine if preset displacements are exceeded.

The sole bar 36 also includes a track obstruction sensor (not shown) and a tire failure sensor (not shown). If these are triggered they are arranged to interrupt power to the electric motor 9.

To allow for differing heights of the pavement 100 to be tested, the centre post assembly 3 may be raised or lowered from its normal horizontal level by a series of packers 50 (see FIG. 5) positioned adjacent the anchoring points 51 for rigidly attaching the centre post assembly 3 to the centre foundation 13. Variations in height of the centre post assembly 3 thus may be achieved by suitable jacking means. Concentricity of the centre assembly during jacking operations is maintained by the centre guide 49.

The wheel arrangement of the road wheel bogey 7 may be altered to correspond to any one of the following in symmetrical or differing combinations:
- a single driven tired van wheel;
- a single driven tired van wheel combined with a single steering tired van wheel;
- a dual tired truck wheel with either one or both tires driven;
- a tandem axled, dual tired truck wheel combination with either one or both tires on either or both axles driven; and
- attachment of supplementary motor car wheels bracketed from the bogies.

By varying the weights 37, actual wheel loads or any combination of the above described wheel arrangements may thus be reproduced.

The fixed displacement motors 10 may be variable displacement motors and set automatically to produce any desired torque/speed characteristic within their range of competence.

Means are provided to monitor the radial position of the arms 6 relative to the centre post assembly 3. Said means may be a helical bar engaging a nut which is fixed to an element of the slide frame which causes the helical bar to rotate as the slide frame moves radially and by its rotation, to drive a rotary encoder.

Road speed and distance travelled by the machine are monitored by proximity sensors which actuate a PID control loop and counters respectively. A bellows cover arrangement (not shown) may be used to protect the slide frame 5 from weather and contamination.

Figure 9:
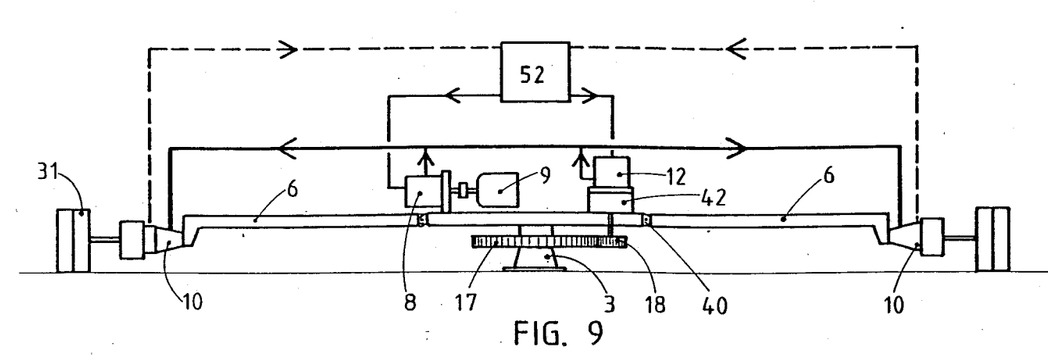
FIG. 9 is a schematic representation of the various driving means of the hydraulic system of the present invention.

The above described pavement testing machine 2 operates in the following manner: the first hydraulic pump 8 is connected hydraulically to each hydraulic motor 10 mounted in the axle housing 11. When power is supplied by the electric motor 9 and the output from the first pump 8 is supplied evenly to the hydraulic motors 10, (if more than one bogey is utilised), rotational movement about the centre post assembly 3 is given to the pavement testing machine 2. The hydraulic fluid after passing through the hydraulic motors 10 returns to a reservoir 52. Rotational speed of the pavement testing machine 2 is then regulated by varying the hydraulic output from the first hydraulic pump 8.

The second variable displacement hydraulic pump 12 is driven from the main gear ring 17 by rotation of the pavement testing machine 2. For flat running modes, the control of the second variable pump 12 remains in neutral. To impose a simulated gradient onto the pavement 100, the control of the second variable pump 12 is proportionately advanced, causing hydraulic fluid drawn from the reservoir 52 to be delivered into the same pipe system as is fed by the first variable volume pump 8. The control of said first volume pump 8 is pre-set such that the output of said pump 8 is adjusted to compensate for hydraulic fluid delivered by said second pump 12.

With said second pump 12 set in neutral there is negligible resistance to the rotation of the pavement testing machine 2. As the second variable pump 12 is activated, it imposes a resisting torque on the rotation of the radial arms 6, resisting the driving force from the wheel motors 10. This produces a combination of vertical and horizontal reactions on the pavement which equates to those produced on the road surface by a vehicle climbing or descending an incline.

At a steady speed of the pavement testing machine 2 and ignoring volumetric efficiency losses, the hydraulic fluid flow rate will remain constant. However the system pressure will rise in direct proportion to the tangent of the gradient angle. It follows that for any given combination of pavement formation, wheel loading and speed, a calculated increment in system pressure serves both as a means of imposing a simulated gradient and of monitoring that gradient.

CONTROL SYSTEM

Under flat running conditions, the first pump 8 can be programmed to give any desired combination of speed, acceleration or braking in combination of up to four modes per revolution of the pavement testing machine 2, or multiples thereof. This can be imposed by means of the speed control loop which is referenced to the rotational speed of the pavement testing machine 2 and is unaffected by variations in volumetric and mechanical efficiency of the pavement testing machine 2 over the range of operating conditions.

Simulated gradients are imposed by a separate control loop referenced to increments in system pressure, above and below those which would pertain if under the particular combination of test track formation, speed and wheel loading, the pavement testing machine 2 was in the flat running mode. The basic system pressure relationship to any one combination of test track formation, wheel loading and speed is first established by trial and recorded as permanent data within the control system. Thereafter, it can be retrieved as a reference curve for controlling simulation of gradients.

Considering the above two control loops together, it will be seen that the first control loop will respond independently to any speed command which it receives; whether on flat running or on a simulated gradient. Its function is to maintain a fluid flow rate through the hydraulic motors 10 which is appropriate to the speed command it has received. The gradient control loop then imposes an increment of pressure over the flat running pressure, which is appropriate to the gradient command it receives. A simulated gradient of desired inclination can therefore be achieved.

Thus it will be seen that the machine is capable of maintaining a commanded road speed independent of all other factors and the energy expended in simulating a road gradient is recovered, less only efficiency losses and the nett energy is returned to the driving circuit. Typically in the gradient mode this allows application to the pavement of 1.6 KW for every 1 KW absorbed into the main pump 8 from the driving motor 9.

Accelerating and braking rates are controlled by varying the ramp angle of the actuator on the first main pump 8. These are hydraulic system responses. Also, an emergency drum brake 48 operated by a suitable fail safe system may be provided. Limitations imposed on the system are the maximum input power from the electric motor 9, the maximum speed at which the pavement testing machine 2 can rotate and the maximum pressure which can be sustained by the hydraulic system.

The control system may be capable of manual operation by manually keying in simple command codes to the on shore computer or of automatic operation by programming a testing regime into the on shore computer. Also, for effecting slow, precise movements of the machine, a portable control pendant equipped with 'forward' and 'reverse' switches may be plugged into a bogey mounted electrical socket. When fitted said pendant automatically suspends all other means of control and will cause the machine to move slowly in the forward or reverse direction when one or the other switch is actuated.

METHOD

The present invention further provides a method of testing and evaluating the durability of paved surfaces, substrates and formations by providing a circular test-track of paved surface 100, on which is operated the above described pavement testing machine 2. This will enable a predetermined wheel arrangement and weight loading to replicate the desired actual wheel arrangement and wheel loading on the traffic bearing surface, and to provide a predetermined pattern of wheel traffic across the test pavement and of presetting the geometry of the axles 32 so that the dynamic responses of the wheels 31 replicate those of actual running conditions; and providing a control and a monitoring system. Said control system may be programmed to run the pavement testing machine 2 for an indefinite period. During this period the control system can be used to operate the pavement testing machine 2 to perform and record a predetermined regime of diverse functions. These functions include:

(a) Accelerating, braking or running at steady speed, each in elements of one quarter cycle or multiples thereof;
(b) Climbing and descending a simulated gradient, in combination with (a);
(c) Varying the distribution of wheel traffic over the breadth of the test pavement 100 in combination with (a) and (b);
(d) Any combination of the above; and (e) Stopping and starting at predetermined times, running for predetermined times or distances and resting for a predetermined time in combination with (a) to (c) above.

Said monitoring system may be programmed to:
(a) Monitor and record data which relates to the loading conditions applied to the pavement 100 and the pavement response;
(b) Record the rate and extent of road surface failure;
(c) Automatically transmit an alarm if the limits of safe working parameters are approached;
(d) Stop the pavement testing machine 2 in the event of severe road breakup, tire failure, track obstruction, out of limit loading, over-temperature or exceeding the limits of safe working parameters or upon unauthorised entry to the testing enclosure;
(e) Maintain a constant transmission to a shore based computer reporting operating modes and status of all systems, the status of all dynamic functions, road surface condition and the status of all safety devices;
(f) Maintain in a computer, a permanent log of all the above functions together with a record of aggregated time and distance run.
(g) Permit monitoring or interrogation of the control system via a conventional telephone connection from a point which is remote from the test site.

ENERGY SYSTEM

The present invention further provides an energy recuperation system. As above described, for flat running modes the control of the second variable hydraulic pump 12 remains in neutral; thus it has no fluid output and imposes very limited resistance to the rotation of the pavement testing machine 2. To impose a simulated gradient onto the pavement 100, the control of the second pump 12 is proportionately advanced, causing fluid drawn from the reservoir 52 to be delivered into the same pipe system as is fed by the first pump 8.

If under this condition the output of the pump 8 is not reduced, then the added flow of fluid to the motors 10 would cause the pavement testing machine 2 to speed up and ultimately, lock up. Accordingly, the controls are so contrived as to back off the output of the pump 8 to compensate for the fluid delivered from the pump 12 and if constant speed is required, then the reduction in output from the pump 8 will exactly equate to the full output of the pump 12 less volumetric efficiency losses.

By this means an average of 80% of the climb energy can be returned to the system. For instance it has been determined that up to 80 KW of power can be applied to the pavement 100 with a system input from an electric motor 9 of 50 KW. The energy absorbed in wind and road resistance and into efficiency losses will always be lost to the system.

Some particular aspects of the invention have been described by way of example and with reference to the accompanying drawings, but it will be appreciated that other variations of and modifications to the invention may take place without it departing therefrom.

What I claim is:
1. Apparatus for testing and evaluating traffic bearing formations and pavements comprising a plurality of bogies provided with different wheel sets to give combinations of from one to six tired wheels per bogey arranged to represent wheels of a range of vehicles; a wheel suspension system for each said bogey comprising vehicle suspension components and so constrained to move in a substantially vertical plane about fixed centres at radii within said bogey that the dynamic responses of said wheels to pavement irregularities substantially replicate the dynamic responses of actual vehicle wheels to actual road way irregularities; means for adjusting the slip angles of the tires of said wheels in relation to said pavement; a driving system for said wheels adapted to apply tractive and braking efforts to said wheels for the vehicle-type which any wheel set represents and which produces unsprung weights for the vehicle represented; means providing for compensation for the deflection of road springs when loaded and for placement of loading weights such that interactions between said tires and said pavement are not distorted by varying the wheel loads and road speed; one or more arms extending radially from a centre pivot at the inner end of said arm(s) and adapted to connect with any of the said bogies types at the outer end to constrain a bogey connected thereto to movement in a generally circular path on said pavement about said pivot during operation of said apparatus; a slide frame connecting the inner end of each radial arm to said centre pivot via a rotating bolster mounted about said pivot, said slide frame(s) being contained within said central rotating bolster and constrained to move only in a radial direction relative to said bolster and movable by rams to move said radial arms and said bogies radially in relation to said centre pivot to vary the path of said wheels carried by said bogies across the test surface; means for providing resistance to rotation of said radial arm(s) about said central pivot to simulate the ascent or descent of a gradient upon said pavement; means for varying the road speed of said wheels between zero and a maximum speed; means for varying the loadings carried by said wheels to correspond to loadings carried by vehicle wheels which said wheels represent; and an electronic control system for the apparatus programmable to cause said apparatus to operate to impose and monitor a predetermined test regime on said pavement, unattended and for an indefinite period.

2. The apparatus as claimed in claim 1 wherein the means for providing resistance comprises a pump coupled to the central pivot so that as said radial arm(s) rotate about the central pivot, the said pump is driven.

3. The apparatus as claimed in claim 2, wherein said pump is connected between said central pivot and said radial arm.

4. The apparatus as claimed in claim 3, wherein said pump provides substantially nil resistive torque to the rotation of said radial arm(s) about said central pivot when the apparatus is in a level running mode and imposes a resistive torque about the central pivot in predetermined increments when running in a simulated gradient mode.

5. The apparatus as claimed in claim 4, wherein the said motor for driving the wheels is a hydraulic motor, and the fluid flow to said motor from said hydraulic pump associated with the central pivot is brought together with the fluid flow from an electrically driven pump to enable power to be extracted by the first said pump and redelivered to said driving motor.

6. The apparatus as claimed in claim 1, wherein the means to vary the vertical force comprises removable weights associated with the road wheel, and means to compensate for height variations introduced by the addition or removal of said weights and further, the placement of said weights in such a manner in relation to other rotating masses that there is substantially no weight transfer between the road wheels and the radial arm attachments under the influence of centrifugal forces.

7. The apparatus as claimed in claim 1, wherein a lockable hinge is provided at approximately mid length of each radial arm to enable the arms to fold in the horizontal plane and thus allow the bogies to be driven off the test track to permit reconstruction thereof; and combined with said hinging arrangement, an 'inching' pendant controller which can be plugged into a bogey mounted electrical socket so to suspend all other means of control and equipped with 'forward' and 'reverse' switches which when actuated, cause the bogey to move slowly in either the forward or the reverse direction; said 'inching' control may also be used for conducting pavement recovery tests (such as Benklemann Beam tests).

8. An apparatus for testing and evaluating road formations and paved surfaces comprising:
a circular test track; a fixed centre post assembly engaging a rotatable centre pin, a bolster attached to said rotatable centre pin and housing a slide frame which has radial movement in relation to the bolster; a radial arm connected by one end in a substantially horizontal plane to one end of the said slide frame; a road wheel bogey connected to the second end of the radial arm; a first driving means mounted on said bolster for providing hydraulic power to a subsidiary driving means; a subsidiary driving means connected to the road wheel or wheels and to the first driving means to produce acceleration, braking and constant speed; a retarding means hydraulically connected with the first driving means to provide resistive torque to the rotation of the radial arm about the centre post; means to recover and reuse a portion of the energy consumed; means to apply differing wheel loads to said road wheel bogey so contrived that the vertical reaction borne by the pavement is substantially independent of road speed; and means to adjust the slip angle of road wheels to compensate for their circular path and to impose the effect of cornering on the pavement.

9. A hydraulic energy recuperation system for the apparatus of claim 4, comprising:
an electrically driven variable volume pump for the delivery of fluid to one or more hydraulic driving motors which together cause the apparatus to rotate in a second variable volume pump which is mechanically driven by the rotation of the machine from which pump the fluid output is combined with that of the first said pump for delivery to the said motors in such a manner as to substantially recover the energy extracted by resistance to the machine's rotation and restore this energy (less efficiency losses) to the driving circuit.

10. The hydraulic energy recuperation system of claim 9, wherein the speed and power output of said hydraulic pumps are controlled by a dedicated computer.

11. Apparatus for testing and evaluating traffic bearing formation and pavements comprising:
one or more arms extending radially from a center pivot, each said arm being adapted to connect to a bogey comprising one or more wheels and to constrain its respective bogey to movement in a generally circular path on the pavement about said pivot during operation of the apparatus;

a plurality of bogies each adapted to be coupled to said arm and comprising differing combinations of one or multiple wheels so as to each represent one or more actual wheels or wheel sets of a vehicle or vehicles;

a wheel suspension system for each said bogey constraining the wheel or wheels thereof to move such that the dynamic responses of the wheel or wheels to pavement irregularities substantially replicate the dynamic responses of actual vehicle wheels to actual road way irregularities;

a driving system for said wheel(s) adapted to apply tractive and braking efforts thereto for the vehicle-type which any wheel set represents, the road speed of the wheel(s) on the pavement being variable between zero and a maximum speed;

an electrical control system for the apparatus arranged to control functions thereof including the driving system to said wheels and the speed and tractive and braking efforts applied thereto; and means for varying the loading carried by said wheels to replicate to loadings typically carried by actual vehicle wheels which said wheels represent by adding or removing weights from said bogey or bogies.

12. Apparatus according to claim 11, including means for compensating for the deflection of the suspension system for each said bogey when loaded with varying loadings, and wherein said bogey or bogies and the suspension system(s) therefor are adapted to support the loadings such that interactions between the tires thereof and the pavement are substantially not distorted by variations in the loadings and road speed of said bogies.

13. Apparatus according to claim 11, including means enabling movement of the bogey or bogies radially in relation to said center pivot to vary the path of said wheels thereof across the pavement and wherein said control system is arranged to cause said bogey or bogies to move radially to distribute the wheel traffic across the test pavement to any desired pattern.

14. Apparatus according to claim 13, including a slide frame connecting the inner end of each said radial arm to said center pivot via a rotating bolster mounted about said pivot, each said slide frame being contained within said bolster for movement only in a radial direction relative thereto to move said radial arms and said bogies radially in relation to said center pivot to vary the path of said wheels across the pavement.

15. Apparatus according to claim 13, including means for causing reciprocating radial movement of said bogey or bogies during rotation of said radial arm(s) to distribute the traffic of said wheels across the test pavement.

16. Apparatus for testing and evaluating traffic bearing formation and pavements comprising:

one or more arms extending radially from a center pivot, each said arm being adapted to connect to a bogey comprising one or more wheels and to constrain its respective bogey to movement in a generally circular path on the pavement about said pivot during operation of the apparatus;

a plurality of bogies each adapted to be coupled to said arm and comprising differing combinations of one or multiple wheels so as to each represent one or more actual wheels or wheel sets of a vehicle or vehicles;

a wheel suspension system for each said bogey constraining the wheel or wheels thereof to move such that the dynamic responses of the wheel or wheels to pavement irregularities substantially replicate the dynamic responses of actual vehicle wheels to actual road way irregularities;

a driving system for said wheel(s) adapted to apply tractive and braking efforts thereto for the vehicle-type which any wheel set represents, the road speed of the wheel(s) on the pavement being variable between zero and a maximum speed;

an electrical control system for the apparatus arranged to control functions thereof including the driving system to said wheels and the speed and tractive and braking efforts applied thereto; including means for adjusting the slip angles of the tires of said wheels in relation to said pavement.

17. Apparatus for testing and evaluating traffic bearing formation and pavements comprising:

one or more arms extending radially from a center pivot, each said arm being adapted to connect to a bogey comprising one or more wheels and to constrain its respective bogey to movement in a generally circular path on the pavement about said pivot during operation of the apparatus;

a plurality of bogies each adapted to be coupled to said arm and comprising differing combinations of one or multiple wheels so as to each represent one or more actual wheels or wheel sets of a vehicle or vehicles;

a wheel suspension system for each said bogey constraining the wheel or wheels thereof to move such that the dynamic responses of the wheel or wheels to pavement irregularities substantially replicate the dynamic responses of actual vehicle wheels to actual road way irregularities;

a driving system for said wheels(s) adapted to apply tractive and braking efforts thereto for the vehicle-type which any wheel set represents, the road speed of the wheel(s) on the pavement being variable between zero and a maximum speed;

an electrical control system for the apparatus arranged to control functions thereof including the driving system to said wheels and the speed and tractive and braking efforts applied thereto; wherein said driving system comprises driving means for driving said wheels to apply tractive and braking efforts thereto and retarding means for providing a resistive torque to the rotation of the radial arms for simulating the ascent of a gradient by said wheels.

18. Apparatus according to claim 17, wherein said retarding means comprises a hydraulic pump coupled between said central pivot and at least one said radial arm such that as said radial arm rotates about said central pivot the said pump is driven, said pump providing substantially nil resistance to the rotation of said radial arms when the apparatus is in a level running mode and imposing said resistive torque at one of a number of possible incremental levels when the apparatus is running in a simulated gradient mode.

19. Apparatus according to claim 18, wherein said driving means comprises a primary driving means hydraulic pump associated with said bolster for providing hydraulic power to subsidiary driving means comprising a hydraulic motor providing to each bogey.

20. Apparatus according to claim 19, wherein the fluid flow to said subsidiary driving means hydraulic motor(s) from said primary driving means hydraulic pump is brought together with the fluid flow from said retarding means hydraulic pump to enable hydraulic power generated by said retarding means hydraulic pump to be utilised in driving said subsidiary driving means hydraulic motor(s).

21. Apparatus according to claim 20, wherein said electronic control system comprises a computer control system arranged to impose and monitor a predetermined test regime by the apparatus on the pavement and wherein said control system controls the operation of said driving means hydraulic pump by reference to the road speed of the bogey or bogies and of said retarding means hydraulic pump by reference to the system hydraulic fluid pressure such that the effect of a simulated particular road gradient angle is imposed on the pavement by maintaining a fluid pressure differential which adds to the system pressure pertaining in the flat running mode, and which equates with that gradient angle.

22. Apparatus for testing and evaluating traffic bearing formation and pavements comprising:
- one or more arms extending radially from a center pivot, each said arm being adapted to connect to a bogey comprising one or more wheels and to constrain its respective bogey to movement in a generally circular path on the pavement about said pivot during operation of the apparatus;
- a plurality of bogies each adapted to be coupled to said arm and comprising differing combinations of one or multiple wheels so as to each represent one or more actual wheels or wheel sets of a vehicle or vehicles;
- a wheel suspension system for each said bogey constraining the wheel or wheels thereof to move such that the dynamic responses of the wheel or wheels to pavement irregularities substantially replicate the dynamic responses of actual vehicle wheels to actual road way irregularities;
- a driving system for said wheel(s) adapted to apply tractive and braking efforts thereto for the vehicle-type which any wheel set represents, the road speed of the wheel(s) on the pavement being variable between zero and a maximum speed;
- an electrical control system for the apparatus arranged to control functions thereof including the driving system to said wheels and the speed and tractive and braking efforts applied thereto; wherein said plurality of bogies comprises two or more separately suspended wheels or wheel sets representing two or more vehicles.

23. Apparatus for testing and evaluating traffic bearing formation and pavements comprising:
- one or more arms extending radially from a center pivot, each said arm being adapted to connect to a bogey comprising one or more wheels and to constrain its respective bogey to movement in a generally circular path on the pavement about said pivot during operation of the apparatus;
- a plurality of bogies each adapted to be coupled to said arm and comprising differing combinations of one or multiple wheels so as to each represent one or more actual wheels or wheel sets of a vehicle or vehicles;
- a wheel suspension system for each said boogey constraining the wheel or wheels thereof to move such that the dynamic responses of the wheel or wheels to pavement irregularities substantially replicate the dynamic responses of actual vehicle wheels to actual road way irregularities;
- a driving system for said wheels(s) adapted to apply tractive and braking efforts thereto for the vehicle-type which any wheel set represents, the road speed of the wheel(s) on the pavement being variable between zero and a maximum speed;
- an electrical control system for the apparatus arranged to control functions thereof including the driving system to said wheels and the speed and tractive and braking efforts applied thereto; wherein at least one bogey comprises two or more separately suspended wheels or wheel sets representing two or more vehicles.

24. Apparatus for testing and evaluating traffic bearing formation and pavements comprising:
- one or more arms extending radially from a center pivot, each said arm being adapted to connect to a bogey comprising one or more wheels and to constrain its respective bogey to movement in a generally circular path on the pavement about said pivot during operation of the apparatus;
- a plurality of bogies each adapted to be coupled to said arm and comprising differing combinations of one or multiple wheels so as to each represent one or more actual wheels or wheel sets of a vehicle or vehicles;
- a wheel suspension system for each said bogey constraining the wheel or wheels thereof to move such that the dynamic responses of the wheel or wheels to pavement irregularities substantially replicate the dynamic responses of actual vehicle wheels to actual road way irregularities;
- a driving system for said wheel(s) adapted to apply tractive and braking efforts thereto for the vehicle-type which any wheel set represents, the road speed of the wheels(s) on the pavement being variable between zero and a maximum speed;
- an electrical control system for the apparatus arranged to control functions thereof including the driving system to said wheels and the speed and tractive and braking efforts applied thereto; wherein each wheel suspension system of each bogey is formed substantially of actual suspension components in an actual vehicle suspension configuration for a vehicle or vehicles which the wheels of the bogey represent.

25. Apparatus for testing and evaluating traffic bearing formation and pavements comprising:
- one or more arms extending radially from a center pivot, each said arm being adapted to connect to a bogey comprising one or more wheels and to constrain its respective bogey to movement in a generally circular path on the pavement about said pivot during operation of the apparatus;
- a plurality of bogies each adapted to be coupled to said arm and comprising differing combinations of one or multiple wheels so as to each represent one or more actual wheels or wheel sets of a vehicle or vehicles;
- a wheel suspension system for each said bogey constraining the wheel or wheels thereof to move such that the dynamic responses of the wheel or wheels to pavement irregularities substantially replicate the dynamic responses of actual vehicle wheels to actual road way irregularities;
- a driving system for said wheel(s) adapted to apply tractive and braking efforts thereto for the vehicle-type which any wheel set represents, the road speed of the wheel(s) on the pavement being variable between zero and a maximum speed;

an electrical control system for the apparatus arranged to control functions thereof including the driving system to said wheels and the speed and tractive and braking efforts applied thereto; wherein a lockable hinge is provided at approximately mid length of each radial arm to enable the arms to fold in the horizontal plane and thus allow the bogies to be driven off the test track to permit reconstruction thereof, and combines with said hinging arrangement, and "inching" pendant controller which can be plugged onto a bogey mounted electrical socket so as to suspend all other means of control and equipped with "forward" and "reverse" switches which when actuated cause the bogey or bogies to move slowly in either the forward or the reverse direction.

26. Apparatus for testing and evaluating traffic bearing information and pavements comprising:
one or more arms extending radially from a center pivot, each said arm being adapted to connect to a bogey comprising one or more wheels and to constrain its respective bogey to movement in a generally circular path on the pavement about said pivot during operation of the apparatus;
a plurality of bogies each adapted to be coupled to said arm and comprising differing combinations of one or multiple wheels so as to each represent one or more actual wheels or wheel sets of a vehicle or vehicles;
a wheel suspension system for each said bogey constraining the wheel or wheels thereof to move such that the dynamic responses of the wheel or wheels to pavement irregularities substantially replicate the dynamic responses of actual vehicle wheels to actual road way irregularities;
a driving system for said wheel(s) adapted to apply tractive and braking efforts thereto for the vehicle-type which any wheel set represents, the road speed of the wheel(s) on the pavement being variable between zero and the maximum speed;
an electrical control system for the apparatus arranged to control functions thereof including the driving system to said wheels and the speed and tractive and braking efforts applied thereto; wherein said electronic control system comprises a computer control system arranged to impose and monitor a predetermined test regime by the apparatus on the pavement.

27. An apparatus according to claim 26, wherein said computer control system includes recording means for recording a comprehensive test program log of any one or more of at least the test loading regime and apparatus operating conditions, environmental conditions, pavement responses, and pavement profiles.

28. An apparatus according to claim 26, wherein said control system is arranged to monitor functions including any one or more of at least, strain in said radial arm(s), vertical displacement of axles mounting said wheels, hydraulic system pressure, oil and motor temperature, rotational speed of the radial arm(s) and bogies, and for tire failure, track obstruction, and to arrest the apparatus in the event a preset limit is exceeded in any of said functions for protection of the apparatus.

29. An apparatus according to claim 28, wherein said electronic control system is arranged to run the apparatus unattended for any desired period of time and to advise a distantly located person in the event of arresting of the apparatus.

30. An apparatus according to claim 28, wherein said control system is so arranged that the test program can be monitored, edited, or recorded from a computer terminal at the location of or remote from the apparatus.

31. An apparatus for testing and evaluating traffic bearing formation and pavements comprising:
one or more arms extending radially from a center pivot, each said arm being adapted to connect to a bogey comprising one or more wheels and to constrain its respective bogey to movement in a generally circular path on the pavement about said pivot during operation of the apparatus;
a plurality of bogies each adapted to be coupled to said arm and comprising differing combinations of one or multiple wheels so as to each represent one or more actual wheels or wheel sets of a vehicle or vehicles;
a wheel suspension system for each said bogey constraining the wheel or wheels thereof to move such that the dynamic responses of the wheel or wheels to pavement irregularities substantially replicate the dynamic responses of actual vehicle wheels to actual road way irregularities;
a driving system for said wheel(s) adapted to apply tractive and braking efforts thereto for the vehicle-type which any wheel set represents, the road speed of the wheel(s) on the pavement being variable between zero and a maximum speed;
an electrical control system for the apparatus arranged to control functions thereof including the driving system to said wheels and the speed and tractive and braking efforts applied thereto, wherein the vertical height setting of the apparatus may be adjusted by raising or lowering of said center pivot to compensate for changes in the level of the pavement resulting from rebuilding or resurfacing thereof.

32. A method for testing and evaluating road formations and paved surfaces, said method comprising providing a circular test track, providing a mix of wheels, wheel arrangements and suspension geometrics each carrying weight loadings to replicate actual wheel arrangements, wheel loadings and pavement reactions of an actual road in normal use and driving said wheels with tractive and braking efforts and providing a predetermined pattern of wheel traffic distribution across the test track, whereby to produce dynamic responses of the wheels which replicate those of typical road traffic, and providing a computer based control and monitoring system arranged to control said wheels to perform a predetermined test regime on the paved surface and to record the results thereof, wherein one half of the paved surface is traversed by one bogey and the other half by another bogey, for comparative testing.

* * * * *